(12) United States Patent
Evans et al.

(10) Patent No.: US 6,872,516 B2
(45) Date of Patent: Mar. 29, 2005

(54) METHODS OF PRODUCING CARBON-13 LABELED BIOMASS

(75) Inventors: Keith Darrel Evans, Brentwood, TN (US); Stanley John Konopka, Franklin, TN (US); Eric Charles Henry, Corvallis, OR (US); William Michael Houston, Gresham, OR (US)

(73) Assignee: Advanced Breath Diagnostics, LLC, Brentwood, TN (US)

( * ) Notice: Subject to any disclaimer, the term of this patent is extended or adjusted under 35 U.S.C. 154(b) by 0 days.

(21) Appl. No.: 10/417,951

(22) Filed: Apr. 16, 2003

(65) Prior Publication Data

US 2004/0208892 A1 Oct. 21, 2004

(51) Int. Cl.$^7$ ............................ A61K 35/80; C12N 1/12
(52) U.S. Cl. ................................ 435/3; 435/4; 435/29; 435/41; 435/257.1; 435/257.3; 424/195.17
(58) Field of Search ........................... 435/3, 4, 29, 41, 435/257.1, 257.3; 424/195.17

(56) References Cited

U.S. PATENT DOCUMENTS

| | | | |
|---|---|---|---|
| 4,087,936 A | 5/1978 | Savins et al. ................ | 47/1.4 |
| 4,235,043 A | 11/1980 | Harasawa et al. ............ | 47/1.4 |
| 4,724,214 A | 2/1988 | Mori ....................... | 435/292.1 |
| 5,137,828 A | 8/1992 | Robinson et al. ........... | 435/292.1 |
| 5,162,051 A | 11/1992 | Hoeksema .................. | 47/1.4 |
| 5,541,056 A | 7/1996 | Huntley et al. ............. | 435/3 |
| 5,700,377 A | 12/1997 | Cox ....................... | 210/724 |

FOREIGN PATENT DOCUMENTS

| | | | |
|---|---|---|---|
| DE | 19820078 | * | 11/1999 |
| EP | 0474790 B1 | | 12/1990 |
| WO | WO 90/15525 | | 12/1990 |

OTHER PUBLICATIONS

Berthold, H. K., et al., "Uniformly —C–labeled algal protein used to determine amino acid essentiaity in vivo", Proc. Natl. Acad. Sci. USA 88, 8091 (1991).

Bram A. v.d. Pas, et al., "Energy yield of respiration on Chloroaromatic Compounds in Desulfitobacterium dehalogenans", App. and Env. Microbiol., 67(9), 3958 (2001).

Klein, P. D., "13C Breath Tests: Visions and Realities", Journal of Nutrition, 131, 1637S (2001).

Bjorkman D.J., et al., "13C–bicarbonate breath test as a measure of gastric emptying", Am. J. Gastroentereol., 88(3), 462 (1993) (Abstract Only).

Irving C.S., et al., "[13C]bicarbonate kinetics in humans: intra– vs. interindividual variations.", Am. J. Physiol., 245(2), R190 (1983) (Abstract Only).

Klein, E.R., Klein P.D., A selected bibliography of biomedical and environmental applications of stable isotopes. V–2H, 13C, 15N, 18O and 34 S, 1977–1978, Biomed. Mass Spectrom. 6(12), 515 (1979) (Abstract Only).

Klein, E.R., Klein P.D., "A selected bibliography of biomedical and environmental applications of stable isotopes. II—13C, 1971–1976", Biomed. Mass Spectrom. 5(5), 321 (1978) (Abstract Only).

Brandner, G, et al., "Optimisation of a cyanobacterial culture used for production of isotopes–labelled recombinant proteins", Biotechnology Techniques, 13, 177 (1999).

Sorensen, P, Flemming, P.M., "A simple and economical algal culture system for stable isotopic labeling", J. of Biomolecular NMR, 2, 99 (1992).

* cited by examiner

Primary Examiner—Herbert J. Lilling
(74) Attorney, Agent, or Firm—Fredricksonson & Byron, PA

(57) ABSTRACT

A method and apparatus for preparing uniform carbon-13 labeled biomass using a water soluble carbon-13 labeled carbon source, such as a [$^{13}$C]-bicarbonate or [$^{13}$C]-carbonate salt, is disclosed. The biomass is prepared in one or more sterile carboys filled with growth medium, in which acidity, oxygen, and biomass density are carefully monitored and maintained. By using a solid, water-soluble [$^{13}$C]-bicarbonate or [$^{13}$C]-carbonate salt as the sole carbon source, a biomass is provided which is uniformly and efficiently labeled with carbon-13. This method and apparatus is particularly useful for the growth of an edible carbon-13 labeled algal mass, with *Spirulina platensis* being a specific alga species. The biomass may be prepared in conformance with FDA current good manufacturing practice regulations, and may be harvested and formed into lyophilized bulk drug powder which may be further processed into various drug product forms which are useful for diagnostic tests or in pharmaceutical compositions.

11 Claims, 6 Drawing Sheets

METHODS OF PRODUCING CARBON-13 LABELED BIOMASS

FIELD OF THE INVENTION

This invention relates generally to methods and apparatus for preparing carbon-13 labeled biomass. In particular, the present invention relates to a method and apparatus for growing carbon-13 labeled digestible algae in a controlled and consistent manner for use as a component of a diagnostic test kit or pharmaceutical composition.

BACKGROUND OF THE INVENTION

Labeled compounds incorporating stable isotopes have been used in the analysis of metabolic pathways and human nutrition, and are becoming increasingly important in disease diagnosis. In isotopic labeling, one or more of the atoms of a molecule of interest are substituted for an atom of the same element, but of a different isotope. Because the atom has the same number of protons, it will behave the same chemically as other atoms in the compound. However, the difference in the number of neutrons imparts a mass difference that can be detected separately from the other atoms of the same element.

Isotopically altered compounds can be easily identified through various techniques, such as nuclear magnetic resonance (NMR), mass spectrometry (MS), or autoradiography. By using isotopically labeled compounds, the metabolic and physical processes occurring in an organism can be studied by observing the path that labeled material takes and the types of metabolic end products that the label is eventually found in. Isotopic labels can be generally divided into two classes; those that are radioactive, such as carbon-14, tritium, and technetium-99 m, and those that are stable, such as carbon-13, nitrogen-15, and oxygen-18. While radioactive labeled compounds can be identified by a greater number of techniques, their use typically requires specialized nuclear medicine facilities and may be contra-indicated in children and women of child-bearing age, thus limiting their usefulness.

Carbon-13 [$^{13}$C] is a particularly useful isotope, as carbon is present in essentially all organic material and $^{13}$C is a non-radioactive isotope that is readily identified. In $^{13}$C analysis, $^{13}$C is introduced into one or more functional groups in a substrate. The functional groups are linked to the rest of the molecule through bonds that are cleaved by specific enzymes. Once cleavage occurs, the functional group is typically further oxidized until $^{13}CO_2$ is produced, which is then excreted in the breath. The appearance of excess $^{13}CO_2$ in respiration can be used to indicate the presence and amount of enzymatic activity or indicate the presence of a foreign substance such as bacteria. This use of $^{13}$C has led to the development of a number of $^{13}$C-based breath tests. See Peter D. Klein, "$^{13}$C Breath Tests: Visions and Realities", *Journal of Nutrition*, 131, 1637S, 2001, the disclosure of which is incorporated herein by reference.

To conduct breath tests, or other tests using $^{13}$C label, a digestible source incorporating the labeled material is often needed. $^{13}$C labeled bicarbonate ingested by a subject in a breath study to measure gastric emptying produced unreliable results when administered without being incorporated into a digestible material. $^{13}$C label incorporated into microorganisms has proven to be a superior vector for introducing labeled material to a subject for breath tests.

Algae are microorganisms that have been found to be useful as a digestible source in breath tests. Algae labeled in this fashion have been defined as a drug by the FDA as have previous substrates for other legally marketed $^{13}$C-labeled breath tests. The proteins, lipids, and carbohydrates of these organisms can be engineered to contain high levels of $^{13}$C label. If such organisms are used, they can be readily introduced for diagnostic and physiological measurements by incorporating them in an edible product such as biscuits. See U.S. Pat. No. 5,707,602, the disclosure of which is incorporated herein by reference, for an example of this approach.

Various single-celled organisms have been cultivated in the presence of a $^{13}$C source in order to provide labeled organisms. To increase the incorporation of $^{13}$C, as opposed to atmospheric $^{12}$C, cultivation of these organisms is typically conducted in a bioreactor, an apparatus that provides the conditions necessary for growth while preventing contamination. Algae are useful organisms for providing $^{13}$C labeled biomass, as the nutrient requirements of algae are relatively inexpensive. To culture algae, it is necessary to provide a carbon source, which is typically $CO_2$ gas, various trace nutrients, and light, which the algae use to drive photosynthesis.

As $CO_2$ gas is the traditional carbon source for cultivating algal biomass, previous efforts to produce $^{13}$C labeled algae have used $^{13}CO_2$ gas as the carbon source. $^{13}CO_2$ gas, however, is relatively expensive and a significant amount may be lost through waste. Also, typically $^{13}CO_2$ gas is bubbled into a growth chamber of a bioreactor. If fittings, seals, and other chamber components fail during the process, $^{13}$C label may be diluted and there is an increased chance of contamination. Even when fittings and seals remain sealed, a significant amount of the $^{13}CO_2$ gas may simply pass through the system without being absorbed into the biomass. Furthermore, while gas volumes can be calculated theoretically, it is difficult to reliably administer precise volumes of gas, such as $^{13}CO_2$. Finally, use of $^{13}CO_2$ gas as the carbon source requires the use of bulky pressurized cylinders that are awkward to transport and handle.

A method of consistently producing a uniformly $^{13}$C labeled biomass without the use of $^{13}CO_2$ gas and its associated contamination, wastage, and handling problems, for use as component of a diagnostic test kit or as an active pharmaceutical ingredient in a drug product would be desirable.

SUMMARY OF THE INVENTION

The present invention, in one embodiment, relates to methods for reliably and consistently producing $^{13}$C labeled biomass for use as a bulk drug incorporated into a diagnostic test kit as a digestible source of labeled carbon. In another embodiment, the present invention provides a $^{13}$C labeled biomass bulk drug that can be formulated into a finished drug product for, among other things, the assessment and/or diagnosis of disease or physiological dysfunction in humans and animals. The method of the invention includes the use of 13C-labeled water-soluble bicarbonate or carbonate salt, or other similarly soluble solid as the carbon source during the growth of the biomass to obtain a substantially uniformly labeled biomass. In one embodiment, $NaH^{13}CO_3$ is used. The water-soluble [$^{13}$C]-bicarbonate or [$^{13}$C]-carbonate salts provide superior saturation of media with carbon source, and are not wastefully passed through the bioreactor without being absorbed by the growing organisms, thus, the labeled biomass is substantially uniformly labeled. Solid carbon sources such as carbonate or bicarbonate salts also have the positive attributes of being compact and relatively stable, simplifying handling issues and are relatively inexpensive to use.

In a further embodiment of the invention, a uni-algal inoculum is used as the starting material with the solid carbon source. The uni-algal inoculum makes use of a single, well-defined algal culture with well-defined growth characteristics. The labeled biomass of the invention is substantially uniformly labeled with a predictable amount of label, and is more readily used in the formulation of a drug because the determination of appropriate unit dosages of the labeled component may be made reliably.

In one aspect of the invention, $^{13}C$ labeled biomass for use in a bulk drug is manufactured by inoculating a growth reactor that includes growth medium including a water-soluble $^{13}C$ carbon source, such as water-soluble [$^{13}C$]-bicarbonate or [$^{13}C$]-carbonate salt, with an organism which will uptake carbon through photosynthesis, then growing and monitoring the growth of the organism until a desired biomass density is obtained, and finally harvesting the resulting $^{13}C$ labeled biomass. The labeled biomass is then incorporated into a bulk drug.

Algae are useful organisms for creating the biomass of the present invention. An edible alga, such as *Spirulina platensis* may be incorporated into a digestible source of labeled material for use in a breath test.

The method of the invention may be readily adapted to comply with the U.S. Food and Drug Administration's Good Manufacturing Practices regulations, currently in effect, as they relate to the manufacture for active pharmaceutical ingredients (API's). Accordingly, the biomass prepared using the methods of the invention may be used as a bulk drug.

In one embodiment, the $^{13}C$ labeled biomass prepared using the method of the invention has an isotopic purity of 90% or more. Further steps in the method may include lyophilizing the biomass and milling the biomass into a uniform bulk drug form suitable for unit dosing in a final drug product.

A further embodiment of the present invention comprises bulk drug including a biomass that is substantially uniformly $^{13}C$ labeled. In one embodiment, the biomass comprises algae. Edible algae are particularly useful when the bulk drug is to be incorporated into a digestible substrate, such as with the species *Spirulina platensis* being useful edible algae in diagnostic breath test kits for gastric emptying. The algal biomass may be lyophilized and milled into the bulk drug (drug material not yet formulated into the final drug product). The $^{13}C$ labeled biomass may have an isotopic purity of 90% or more.

An additional embodiment of the present invention comprises a growth reactor system that may be used to cultivate $^{13}C$ labeled biomass of the invention. The system includes one or more carboys, wherein each carboy is sealed at its open end with a cap. The ports include a sampling port, a dosing port, and a venting port. When two or more carboys are used in the growth reactor system, they are typically isolated so as to preserve individual carboy axenicity in the event that a single carboy is contaminated. The system may further include means for operating the growth reactor under conditions of pass-through illumination of about 1000–2000 Lux and at a temperature of about 29–31° C. Additionally, means for monitoring and maintaining the pH of the growth media at a desired pH and preventing oxygen buildup may be included in the system.

BRIEF DESCRIPTION OF THE DRAWINGS

The invention will now be described by way of example with reference to the accompanying drawings wherein.

DETAILED DESCRIPTION OF EMBODIMENTS OF THE INVENTION

Figure 1:
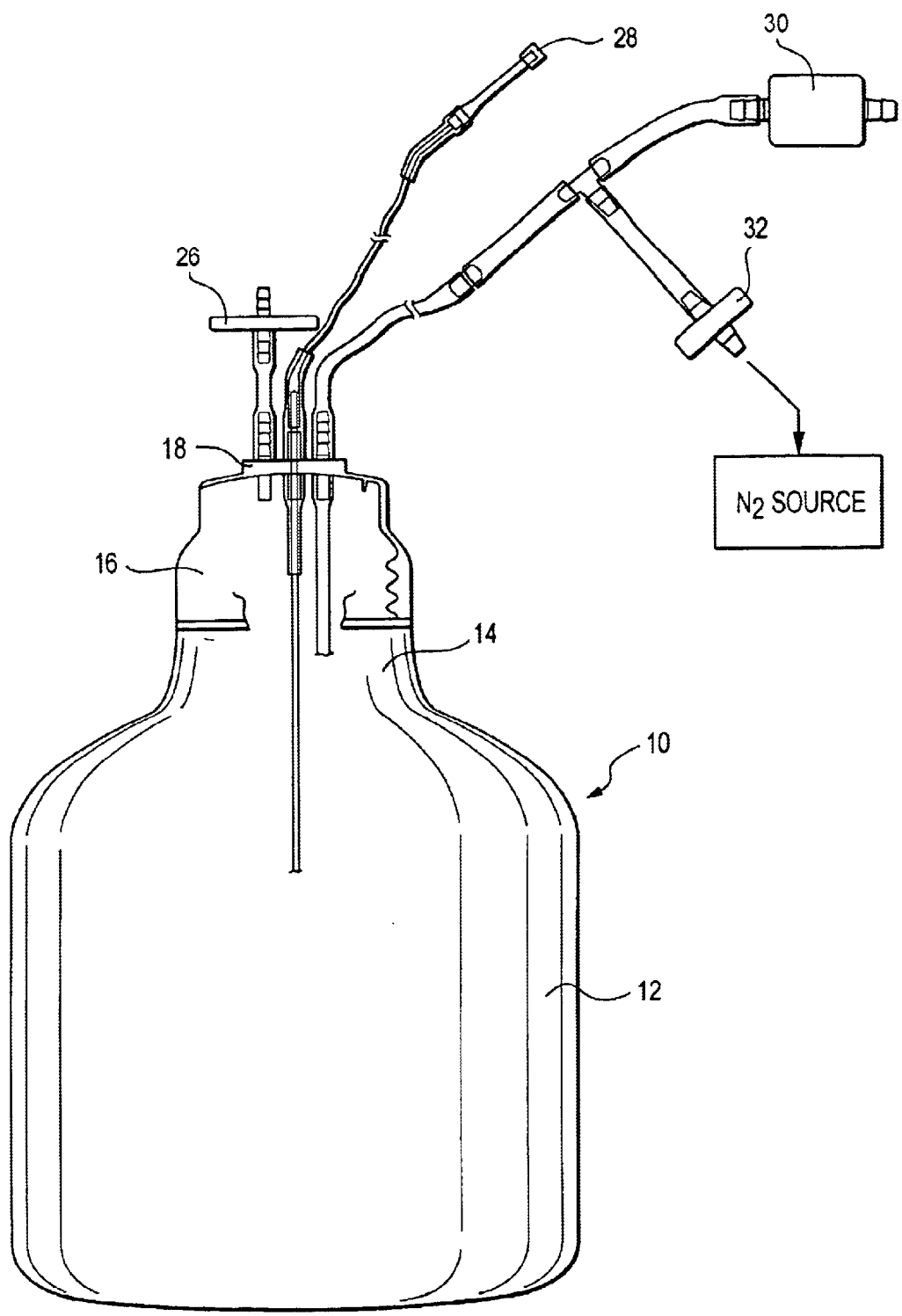
FIG. 1 is a side view of an embodiment of a carboy growth reactor.

Carbon-13 is a non-radioactive, stable isotope marker useful in pharmaceutical and diagnostic devices. Approximately 99% of all carbon in nature, including the carbon in our bodies and the food we eat, is carbon-12. By synthesizing molecules or growing organisms containing biomolecules rich in $^{13}C$, one can take advantage of the fact that their absorption and metabolism results in the release of respiratory $^{13}CO_2$. Breath samples can be obtained prior to administering a $^{13}C$-labeled substrate in humans or animals. The ratio of $^{13}CO_2/^{12}CO_2$ can be measured by gas isotope ratio mass spectrometry or other methods of lesser precision and accuracy such as infra-red. After administering the $^{13}C$-labeled substrate, breath samples can again be collected and the $^{13}CO_2/^{12}CO_2$ ratio determined. Increases in the post-dose ratio, or a lack thereof, are valuable in identifying disease and/or measuring biological and physiological processes.

An important aspect of diagnostic tests using $^{13}C$ is that the amount of $^{13}C$ administered must be precisely known. For example, in a breath test, the results are based on the amount of $^{13}CO_2$ produced, which is directly related to the amount originally ingested. To determine the actual dosage of $^{13}C$ in biomass, it is necessary to know the weight percentage of carbon, as well as the percent of the carbon that is $^{13}C$. This is shown in Table 1, which shows three different amounts of $^{13}C$ label target dosages for the alga species *S. platensis*. The amount of $^{13}C$ labeled *S. platensis* biomass which must be administered to achieve the target dose of $^{13}C$ is determined according to the following equation:

Target Dosage mg $^{13}C$ ÷ ($^{13}C$-Atom %×Carbon %)=mg [$^{13}C$]-*S.platensis* dispensed.

Table 1 below provides several examples of how the equation is used.

TABLE 1

Example calculation of dispending to achieve three target dose levels of $^{13}C$.

| Target Dose Mg $^{13}C$ | [$^{13}C$]-S.p. $^{13}C$-Atom % | [$^{13}C$]-S.p % Carbon | [$^{13}C$]-S.p. mg | Tolerance ± mg |
|---|---|---|---|---|
| 80 | 0.95 | 0.42 | 200 | 20 |
| 40 | | | 100 | 10 |
| 20 | | | 50 | 5 |

An advantage of the present invention is that it simplifies the determination of target dosage from biomass, since the biomass prepared using the method of the invention will be substantially uniformly labeled with predictable carbon and $^{13}C$ incorporation levels. For the embodiment utilizing *S. platensis*, the carbon content will generally be about 42%, and the $^{13}C$ incorporation about 95%, as shown in the table above.

The present invention is directed to a method and apparatus for the growth of $^{13}$C-labeled biomass. The labeled biomass may be used as a substrate for the breath test described above or as bulk drug used in the preparation of such a substrate. In addition, the $^{13}$C-labeled biomass may also be employed otherwise as is known to the art. Biomass may be provided using various algae and other microorganisms. *Spirulina platensis* is a useful organism for the cultivation of $^{13}$C-labeled biomass.

The term "biomass" as used herein includes all organisms capable of photosynthetic growth such as plant cells and microorganisms (including algae) in unicellular or multicellular form that are capable of growth in a liquid phase. The term may also include organisms modified artificially or by gene manipulation. Biomass may also be used herein to refer to the amount of living matter (as in a unit area or volume of habitat).

Bulk drug, as used herein, means a substance (e.g., $^{13}$C-labeled *Spirulina* biomass) intended to be used in the manufacture of a drug product that, when used in the production of a drug, becomes an active ingredient of the final drug product. Such substances are intended to furnish pharmacological activity or other direct effect in the diagnosis, cure, mitigation treatment, or prevention of disease or to affect the structure and function of the body. The material can be further processed into a variety of specific finished drug product forms if desired.

Algae, including *Spirulina platensis*, require for their growth water, illumination, a carbon source, and certain other nutrients and nutrient-related materials. The illumination may be sunlight, i.e. solar radiation, or a prescribed bandwidth of artificial illumination. To produce a biomass of algae that are obligate photoautotrophs, such as *Spirulina platensis*, the source of carbon has typically been gaseous carbon dioxide supplied to a bioreactor or biomass in admixture with air. Typically, the growth medium, includes, in addition to the carbon source, which may be added as gaseous carbon dioxide, a distribution of macro and micro levels of inorganic ions, chelating agents, buffering agent, etc.

Photosynthesis is the primary route by which carbon is incorporated into biomass in the present invention. Photosynthesis is used by green plants and certain other organisms to synthesize carbohydrates from carbon dioxide and water using light as the energy source. This process converts light energy into chemical energy, which can be used by the organism in a variety of ways. The conversion of $CO_2$ into organic compounds (such as carbohydrates) is known as carbon fixation, and is represented by the balanced equation below:

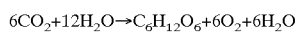

$$6CO_2 + 12H_2O \rightarrow C_6H_{12}O_6 + 6O_2 + 6H_2O$$

The present invention uses as a carbon source, an easily handled water-soluble carbon-13 labeled solid, such as a [$^{13}$C]-bicarbonate or [$^{13}$C]-carbonate salt. 13C-labeled compounds and materials are available commercially. For example, $^{13}$C-labelled $NaHCO_3$ useful as a carbon source in the method of the invention is currently commercially available from Cambridge Isotope Laboratories, Inc. with a $^{13}$C incorporation purity of >=99%. $NaH^{13}CO_3$ is a non-toxic, white crystalline powder that dissolves readily into water. At 25° C., $NaH^{13}CO_3$ is soluble in water to the extent of 1.0 g/10 ml of water. Thus, it can be readily dissolved in the aqueous media used in a biomass growth reactor.

As discussed above, $^{13}$C-labeled biomass prepared using a water-soluble solid such as a [$^{13}$C]-bicarbonate ($NaH^{13}CO_3$) or [$^{13}$C]-carbonate salt as a sole source of carbon during the growth of biomass results in a more substantially uniform biomass. Furthermore, the $^{13}$C label is protected from loss or dilution during the growth cycle of the biomass by the inherent solubility of $^{13}$C-labeled salt in the growth media, which results in a reduced need for adding additional labeled carbon during the growth process. Thus, loss of relatively expensive $^{13}$C label is minimized.

In one embodiment, a single-species, single source starting inoculum (i.e. uni-algal inoculum) is used to initiate biomass growth and to yield a biomass with more consistent carbon levels, $^{13}$C-label percentage, and digestability characteristics. Fatty acid methyl ester (FAME) analysis can be performed on the harvested biomass to assure that the genus and species of the biomass have remained consistent with the genus and species of the starting inoculum throughout the growth process.

Using the method of the invention to prepare $^{13}$C-labeled biomass, the conditions of the growth cycle may be controlled so that the total carbon content and isotope labeling percentage of the biomass will be consistent. These levels can be precisely measured from batch to batch, and to allow for a precise unit dosing of bulk drug into drug product derived from successive batches of labeled biomass. Small variances in the total carbon content and/or the percentage of $^{13}$C label can be adjusted for in the unit dose manufacturing process. For example, a targeted 100 mg unit dose with 45% carbon content and >=95% $^{13}$C label can always be obtained by making small adjustments up or down in the biomass weight target used in the unit dose packaging process, because both carbon parameters can be precisely quantified upon assay of the finished, dried and milled bulk biomass.

The process for growing the algae utilizes various means to control pH and oxygen levels, such as using unsparged carboys on a shaker, purging excess $O_2$, monitoring $O_2$ production, measuring $O_2$ production of algal cultures with the Teledyne gas-phase sensors, and controlling pH by progressive addition of phosphate. The process for producing labeled biomass of the invention can be done on a variety of scales, both with respect to label content and with respect to biomass yield.

The labeled biomass of the invention may be produced in a bioreactor system including one or more carboys. Carboys are sterile, jug-shaped containers with specific hardware for biomass cultivation. A wide variety of carboy sizes and shapes are suitable for use in the present invention. The carboys may be constructed of any inert material known in the art such as glass or plastic. The carboys are filled with aliquots of freshly prepared growth medium, and then inoculated with aliquots of starter inoculum. Thus, if a biomass of 40 grams is desired, a single carboy may be inoculated with the chosen biomass species in a growth medium including an amount of water-soluble solid, such as [$^{13}$C]-bicarbonate or [$^{13}$C]-carbonate salt, calculated to achieve a biomass density of 2 grams per liter in the carboy prior to harvesting. If 160 grams are desired, four 20 L carboys can be grown simultaneously as one batch.

The percentage of label incorporated can likewise be controlled. For example, if one desires a biomass with a high label content, the sole source of carbon for both the inoculum and the carboy growth process should be water soluble [$^{13}$C]-bicarbonate or [$^{13}$C]-carbonate salt with a >=99% $^{13}$C label concentration. If a lesser percentage of $^{13}$C label is desired, the labeled salts may be diluted with unlabeled salt to obtain the desired percentage of $^{13}$C label.

Bacterial contamination can be a serious problem when growing algal biomass. Axenicity, or lack of bacterial contamination, is maintained by several methods. First, a single axenic algal growth inoculum is used for each independent carboy growth reactor. All components of the growth reactor are desirably thoroughly autoclaved before use. While multiple carboys may be run simultaneously as a batch, each carboy is maintained in isolation as a closed system.

The purity of final product in terms of isotopic labeling can be determined by a variety of means known in the art. The high isotopic purity of $^{13}C$ often makes the direct analysis of levels of $^{13}C$ in the material difficult, since approximately 98% of the carbon atoms may be $^{13}C$. Gas Isotope Ratio Mass Spectrometry, one method of determining purity levels, is designed to measure low levels of $^{13}C$ content from natural samples where only 1–2% $^{13}C$ is usually present. If this method is used, typically the user will dilute the $^{13}C$ with a well-defined material containing a $^{13}C/^{12}C$ ratio close to the natural abundance (around 1%) in order to decrease the isotopic fraction of the $^{13}C$ to an analyzable level. Note that an advantage of the present invention is that it produces uniform and predictable $^{13}C$ levels and incorporation, which minimizes the amount of analysis of product necessary.

FIG. 1 shows a side view of a 20 L carboy growth reactor 10 useful in the invention. The carboy growth reactor flask illustrated has two sections; the carboy body 12, and the carboy neck 14. The carboy body 12 is generally a truncated cylinder, while the carboy neck 14 comprises a reduced diameter cylinder adjoined to the carboy body 12 by a rounded conical portion, open at the top. The carboy neck 14 is preferably threaded to securely retain carboy cap 16, which seals the top of the carboy growth reactor 10. Centered on the top of the carboy cap is port assembly 18 containing one or more apertures through which the interior of the carboy growth reactor 10 can be accessed without compromising axenicity. Port assembly 18 is illustrated in more detail in FIG. 2. As noted above, before being used in a method of the invention, to minimize contamination all apparatus that may come into contact with the biomass or any component used to grow the biomass are desirably sterilized. Autoclaving the apparatus is typically the means of sterilization.

Figure 2:
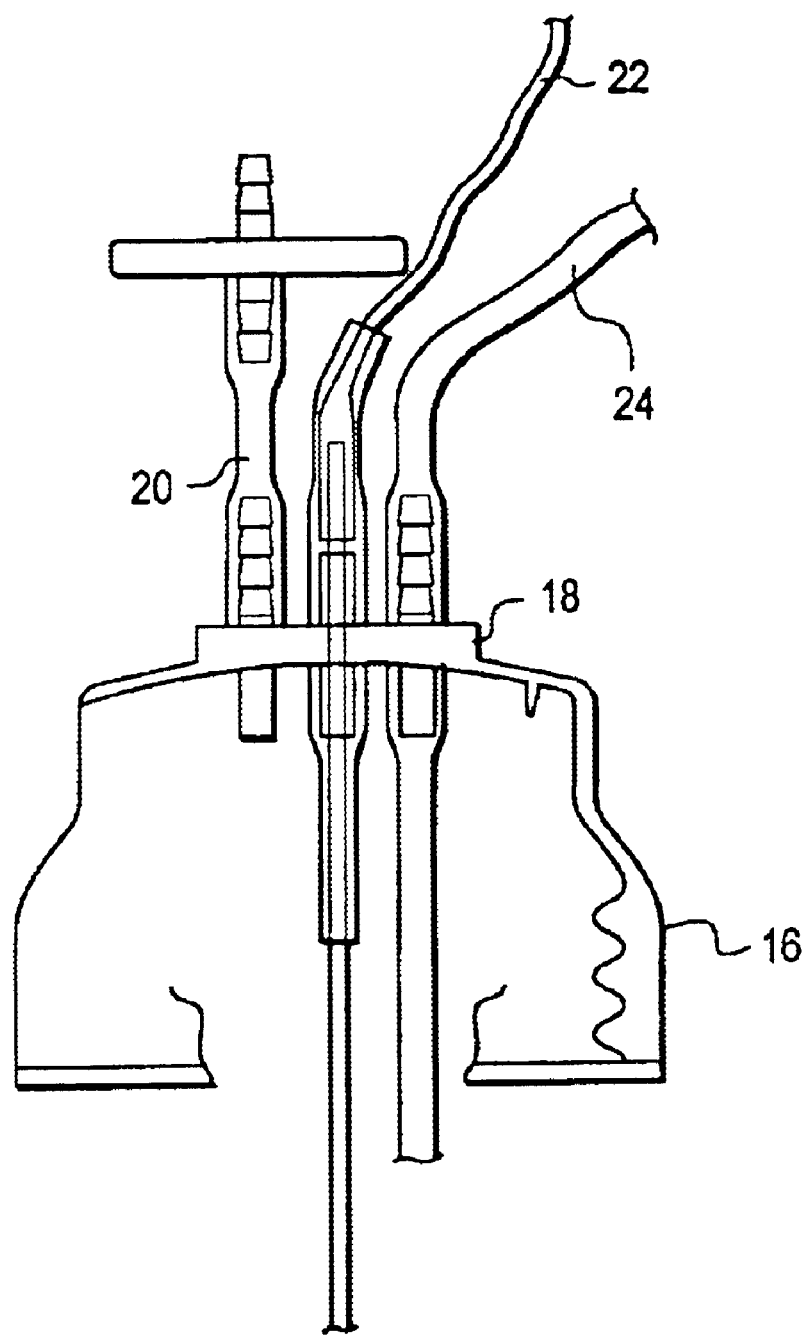
FIG. 2 is a side view of the carboy growth reactor opening configured for the growth phase, showing the carboy cap and its various ports.

In one configuration shown in FIG. 2, three lines lead to the carboy growth reactor 10 through apertures mounted on the port assembly 18. One line is venting line 20. The venting line may be used to allow excess gasses produced by the biomass to be removed from carboy growth reactor 10 before they have an adverse affect on organism growth. A second line is sampling line 22. This line may be used to obtain samples from within the carboy body 12, generally for in-process testing purposes. The third line shown is dosing line 24. The dosing line 24 may be used to add buffer or other useful solutions to media within the apparatus, during the growth process, and may connect to a nitrogen gas ($N_2$) source (not shown) which can be used purge the system of excess oxygen. The gas lines may each be provided with sterile gas filters 26 and 32. Sampling line 22 as shown in FIG. 2 is provided with a sample line cap 28 used to seal the line when not in use. Dosing line 24 may also be provided with a sterile liquid filter 30. Silicone tubing may be used for lines 20, 22, and 24.

Carboy growth reactors useful in the method of the invention may be provided with a vent port. When algae biomass is prepared, $O_2$ is generated during the growth process. The oxygen will typically be vented to the outside via a one-way exit port. If $O_2$ is not vented away from the growth reactor or removed from the reactor by other means, algal burn, comprising impeded growth and oxidative damage, may ensue.

Figure 3:
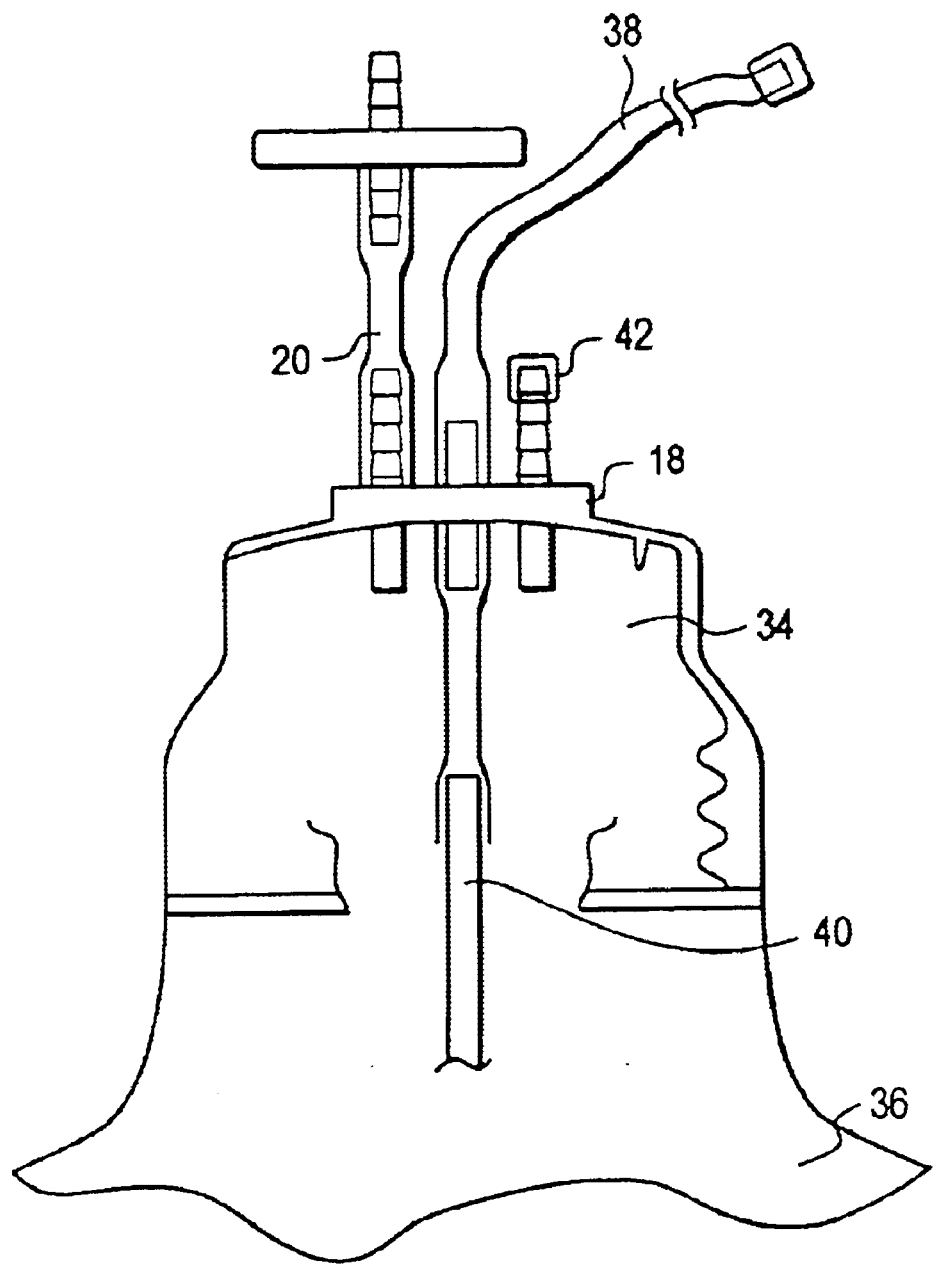
FIG. 3 is a side view of the inoculation carboy assembly, showing the carboy cap and its various ports.

FIG. 3 illustrates an inoculation assembly 34 useful with the invention, assembled at the top of a 10 L carboy which may serve as an inoculation vessel 36. The top of the inoculation assembly may include a port assembly 18 with one or more apertures for access to the interior of the inoculation vessel 36. The port assembly 18 is shown in FIG. 3 as having three apertures. One aperture is connected to venting line 20, which allows excess gas to be released from the inoculation vessel. The venting line may be supplied with a sterile gas filter (not shown). The central aperture illustrated in FIG. 3 as 38 may be an inoculation line. This line may be used initially to fill the inoculation vessel. Inoculation line 38 is connected through the aperture and additional tubing to sterile pipette 40 which extends into the lower portion of the inoculation vessel. The bulk of the liquid may be aseptically removed from the inoculation vessel when desired through the sterile pipette. The third aperture, as any of the apertures, may not be used for a particular method and may be sealed with a cap 42. By means of the inoculation line 38, biomass-containing media from flasks may be prepared in advanced and aseptically transferred into the inoculation vessel, through any known means such as the use of a peristaltic pump.

Figure 4:
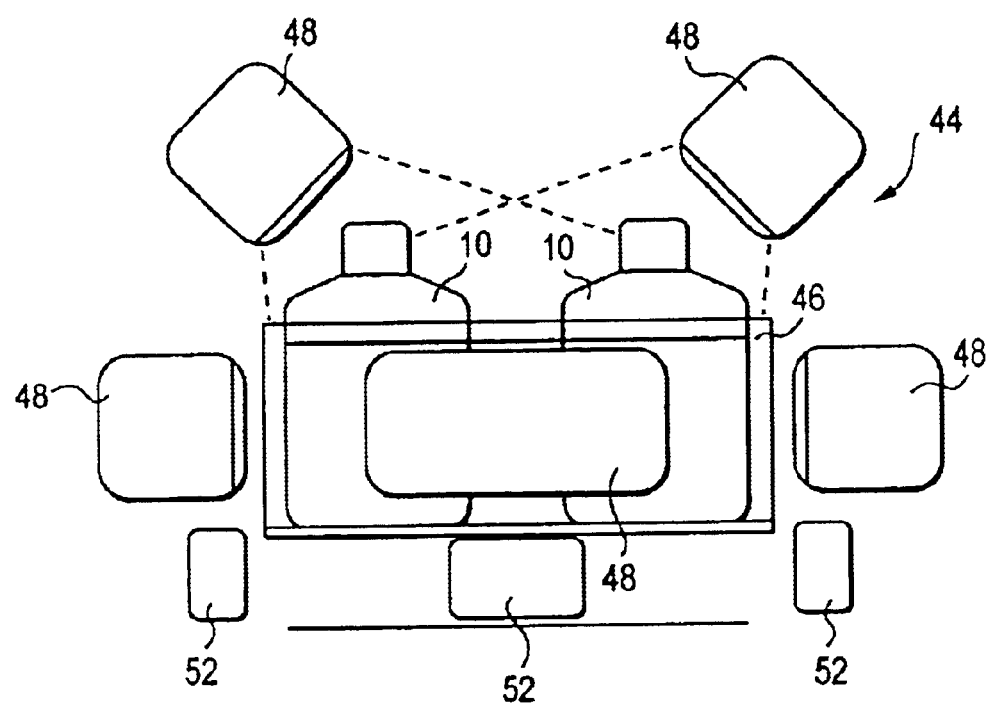
FIG. 4 is a side view of the growth reactor assembly.
Figure 5:
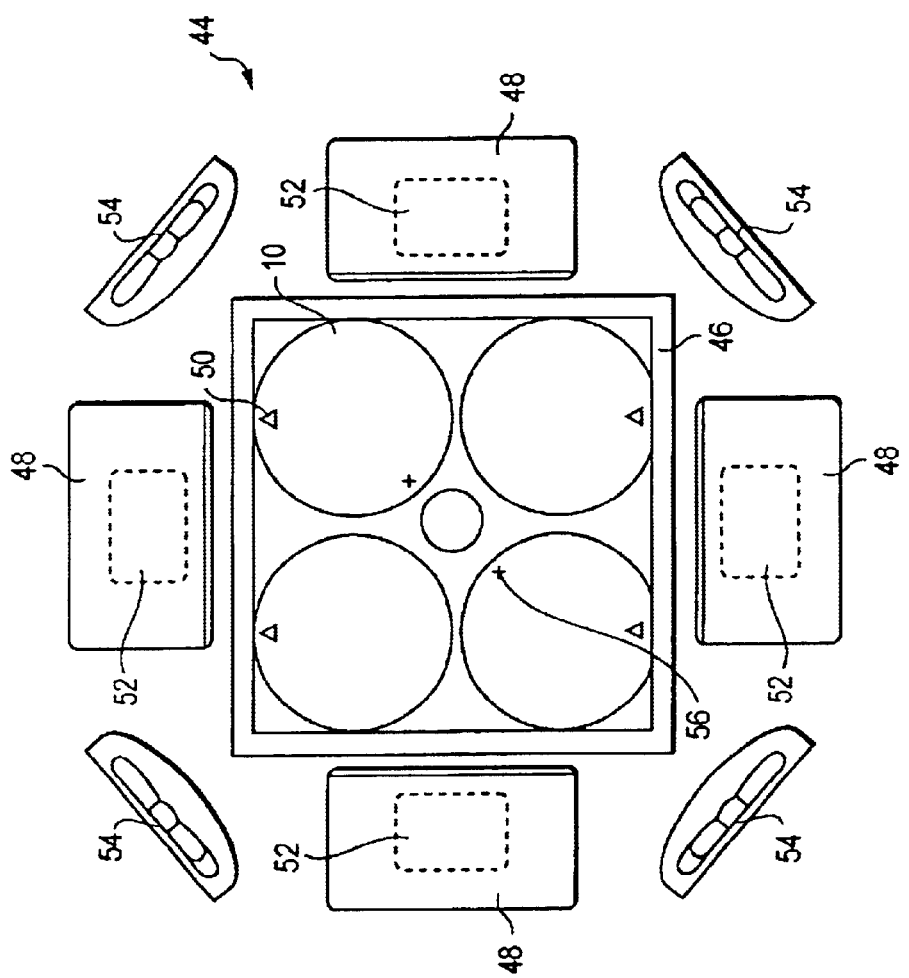
FIG. 5 is a top view of the growth reactor assembly.

Once the growth reactor carboys have been prepared, they may be placed on a rotary shaker table assembly 44, a specific embodiment of which is illustrated in FIGS. 4 and 5. Means of shaking biomass materials during the growth cycle are well known in the art. The rotary shaker table assembly 44 of the bioreactor system exemplified herein, is designed to provide the illumination, motion, and maintain the temperature of the growth medium necessary to stimulate optimal biomass growth, while maintaining the axenicity of the system. As shown in FIG. 5, four carboy growth reactors 10 may be secured and supported on the shaker platform 46 to prevent independent movement from the shaker platform 46. A shaker platform 46 which is a square with 28" sides will support four 20 L carboys such as those shown in FIG. 1. The shaker platform 46 is rotated (i.e. performs circular displacement or "gyrorotary" shaking) at about 80 rpm or other appropriate speed that will maintain even lighting and temperature within the carboy growth reactors 10.

As shown in FIG. 4, lamps 48 may be arrayed around the carboy growth reactors 10 to provide sufficient illumination. While a variety of lamps and illumination arrangements will satisfy these requirements, a specific embodiment of the present invention utilizes six lamps 48, arranged so that four of the lamps are placed on a plane defined by the surface of the shaker table 46, at 90° of separation from each other, while two additional lamps 46 are suspended in "stadium" fashion above two opposite lamps 48, so that they shine down on the shaker table 46 from about a 45° angle relative to the plane created by the lower four lamps 48. A suitable type of lamp is a source that provides light of a quality rich in a bandwidth of wavelengths that favors maximum biomass production. In one embodiment, a level of illumination sufficient to create a pass-through illumination level of 1000–2000 Lux is provided until the carboy growth reactors become opaque.

The amount of illumination applied to the biomass during the growth cycle may be measured by any means well known in the art. FIG. 5 illustrates the use of light transmittance probes 50 that may be placed on the exterior of the carboy growth reactors to measure the amount of light being received. A useful placement arrangement for the light transmittance probes 50 is shown in FIG. 5. The illumination level is based on the amount of light that is transmitted or "passed-through" the growing algae culture and sensed by the probe. One particular type of lamp suitable for this invention is a 400 Watt high pressure sodium vapor lamp. The lamps 48 may be turned on in pairs or other groupings or in sequence to maintain the desired illumination for biomass growth.

The temperature of the bioreactor system during the growth cycle is desirably monitored and controlled. Any means of controlling temperature may be used such as placing the system in an incubator or the like. As shown in FIG. 5, heaters 52 may be provided in order to maintain the carboy growth reactors 10 at the desired temperature. Heaters 52 would be used in the early stages of post-inoculation growth in this system until full lighting provides sufficient heat. Forced air heaters such as the 1000 Watt Heatstream (AdobeAir) may be used in this role. In the embodiment shown in FIGS. 4 and 5, one heater 52 is placed underneath each of the four lower lamps 48. The heaters 52 are preferably monitored by temperature probes 56 that maintain temperature in the carboy growth reactors 10 in the range of about 29–31° C., although the desired temperature may vary among different types of biomass or to vary the growth parameters.

Other means of controlling temperature are well known in the art. As shown in FIG. 5, fans 54, such as 16" oscillating stand fans, may be placed strategically around the rotary shaker table assembly 44 to maintain an even temperature throughout the system during the growth process. Note that if oscillating fans are used, they should preferably not be used in oscillating mode.

Once the starting inoculum has been added to the bioreactor system, in-process sampling and testing may be conducted at regular intervals to determine and monitor the level of growth, whether or not appropriate growth conditions are being maintained, and to detect possible contamination. As shown in FIG. 2, in-process sampling may be done in the bioreactor system shown, through the sample line 22. Such sampling is usually initiated when the carboys growth reactor 10 have become opaque due to biomass growth. Samples may be tested for pH, appearance, density, presence of aerobic bacteria, yeast and/or mold. For growth of algal biomass, the media within the carboy growth reactors 10 will desirably be maintained at a pH of between about 9.5 and 10.5. A suitable buffer, such as 1M monopotassium phosphate buffer may be added as necessary when the pH thresholds are exceeded.

If multiple growth reactors are run concurrently to form a larger batch, carboy sampling may be rotated to minimize culture contact. The sampling measurements on one are closely representative of the others given similar light transmission through the growth reactors.

The sampling port, as well as any other ports into the system, will be designed to maintain axenic conditions within the growth reactor system. All ports, except the sampling port, are typically protected by sterile filters. In addition to providing access for monitoring devices, the venting port may be utilized for introducing sterile filtered $N_2$ gas which is used to flush the carboy head space during times of high oxygen generation. This again serves to prevent algal burn and the associated problems. Monitoring the oxygen generated during algal growth is useful to prevent burn, and is also helpful in assessing the rate of growth in the bioreactor and assessing the growth endpoint as oxygen generation declines.

The system may include other means for measuring pH within the growth reactor such as a sterilized pH probe included as a pre-assembled component within the growth reactor. To maintain the pH through the growth cycle, a dosing port, such as that described above, may be provided. The dosing port allows for the addition of sterile, filtered buffer solution.

In the bioreactor system described herein, a nitrogen purge, in which $N_2$ gas is made to flow through the carboy growth reactor 10, is may be conducted on a regular basis. A gas flow rate of 2 L per minute for 5 minutes provides useful purging.

In a method of the invention, using the bioreactor system described herein, harvesting of the biomass is usually initiated when the culture has reached a density of >2.2 g/L, or 40–44 grams of biomass per carboy.

Figure 6:
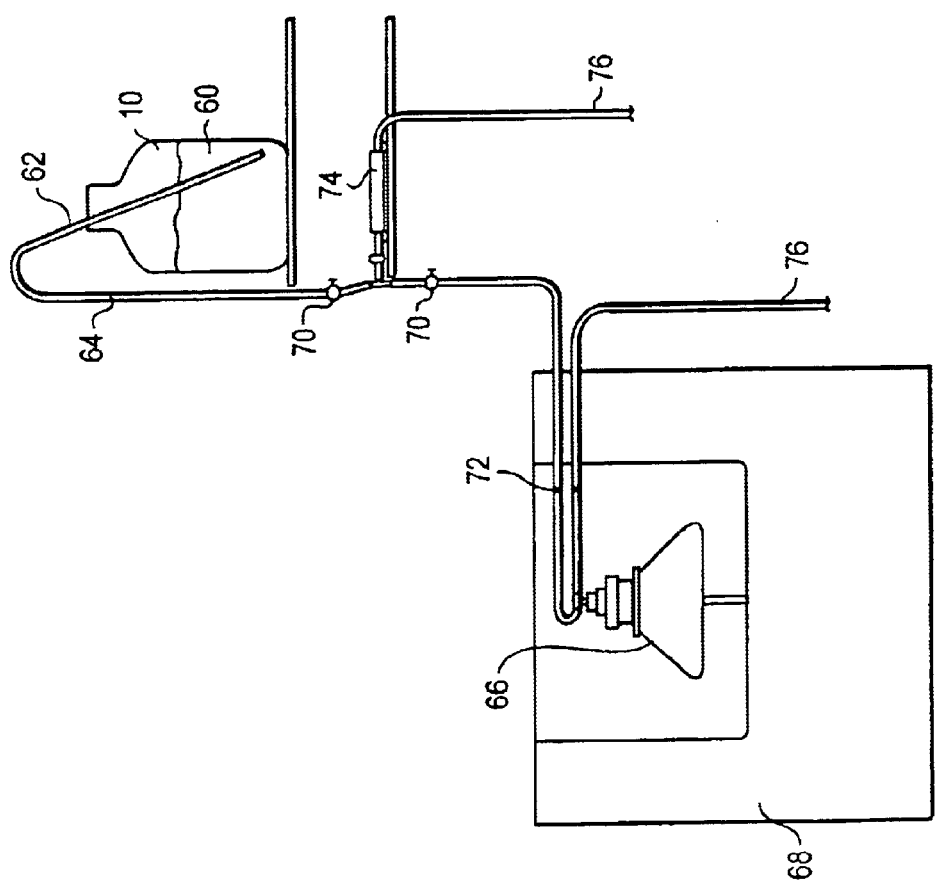
FIG. 6 is a side view of the harvesting assembly.

An apparatus that may be used to harvest biomass is illustrated in FIG. 6. One or more carboy growth reactor 10 are supported in an elevated position. Elevation of the carboy growth reactor 10 above the centrifuge provides flow of the growth medium with biomass by siphon. In the harvesting apparatus shown, the biomass-containing medium 60 is withdrawn from the carboy growth reactor 10 by means of a dip tube 62 that rests within the carboy growth reactor 10. Tubing 64, such as ¼" silicone tubing, is used to transport the biomass-containing medium 60 from the carboy growth reactor 10 to a flow-through centrifuge assembly 66, which is held within a centrifuge apparatus 68, typically refrigerated to about 5° C.

Movement of the biomass-containing media 60 through the tubing 64 is initiated by means of a pump 74, which may be a vibratory pump. Once the fluid is in motion, it will continue without assistance of the pump, due to siphoning action. Flow of fluid through the tubing 64 is usually regulated to 150–350 mL/min. in this apparatus by adjusting a feed line clamp. Two waste lines 76 are present to drain off processed media. Harvesting of biomass within the centrifuge is conducted until all possible material has been retrieved. The presence of biomass organisms within the effluent within the waste lines 76 is generally a signal that the flow-through centrifuge assembly 66 is full, or that the flow rate needs adjustment. The biomass obtained from the flow-through centrifuge assembly 66 is combined into larger centrifuge bottles, with 750 ml centrifuge bottles being a specific size. Material in these bottles is washed and re-centrifuged to obtain biomass that is ready for the final processing steps.

Once the carboys have been inoculated, the growth phase occurs during which proper conditions must be maintained to support optimal biomass growth. The primary elements that must be maintained during this phase are proper illumination, agitation of the growth medium, axenicity, and maintenance of desired temperature and pH. Access to the growth media is done aseptically through the carboy ports, as described above.

Upon reaching the desired biomass density, the biomass is harvested, washed, and reconstituted into a slurry. In preparation for freeze-drying, the liquid slurry is prepared to a desired density, poured by weight into pre-sized containers to hit pre-established target container depth, and frozen at −20° C. to form frozen biomass cakes suitable for lyophilization. A range of frozen biomass cake sizes, densities, and depths are suitable for lyophilization for pharmaceutical processing. The biomass may be prepared for lyophilization in a controlled manner and dried to completion under a pre-established freeze-dry protocol, assuring uniformity in the physical properties of the dried cakes.

Lyophilization is conducted to an extent necessary to dry the product to a very low water level content, and more importantly, low water activity. Water activity is a measure of the free unbound water in the finished product that is available to microorganisms, and is a critical factor in determining the shelf life of the algal mass and its propensity for spoilage by bacteria, yeast, and/or mold. By attaining a specific water activity level, the biomass stability, product integrity, and diagnostic performance are maintained at high levels. Water activity is expressed as % ERH/100-percent equilibrium relative humidity/100. Most bacteria do not grow at water activities below 0.91 and most molds cease to grow at water activities below 0.80.

Once a lyophilized biomass has been prepared, in may be screened and/or milled to yield a biomass with a particle size and texture suitable for unit dose packaging as a finished drug product. The lyophilized and milled biomass is suitable for introduction into solid or liquid food as a physiologic or diagnostic marker for measuring gut motility, gut absorption, metabolic pathways, organ function, efficacy of drugs affecting such functions, and a wide variety of other tests requiring the use of a non-radioactive isotopic marker.

Biomass prepared according to the general fashion above can readily be accomplished while following the current good manufacturing process requirements of 21 CFR 210 and 21 CFR 211, and is suitable for production of biomass meeting the FDA's definition of a drug for human use. Bulk drug including the biomass of the present invention is suitable for use in the Gastric Emptying Breath Test (GEBT), which is described in U.S. Pat. No. 5,785,949, the disclosure of which is incorporated by reference herein. Bulk drug according to present invention will be substantially uniform. This indicates that the bulk drug will have a consistent and predictable carbon level, 13-C label percentage, and digestability characteristics. These desirable attributes lead to useful and consistent results when used in tests such as the GEBT noted above. Note that while the method of the present invention provides bulk drug with consistent and predictable characteristics, it is still preferable to test the precise characteristics of a given batch of bulk drug.

In one embodiment of the present invention, multiple carboys are run simultaneously but independently during the growth of a batch of biomass. The use of multiple, independent carboys allow a large volume of biomass to be prepared without risking catastrophic loss of the entire batch if contamination occurs. For example, if one carboy in a set of 4 carboys becomes problematic, growth of the batch in the three remaining carboys can continue while the problematic carboy is tested for contamination or suitability, and discarded if necessary.

The invention will be further described with reference to the following non-limiting Example. It will be apparent to those skilled in the art that many changes can be made in the embodiments described in the Example without departing from the scope of the present invention. Thus the scope of the present invention should not be limited to the embodiments described in this application, but only by the embodiments described by the language of the claims and the equivalents of those embodiments.

EXAMPLE

Preparation of a $^{13}$C-Labeled BioMass of *Spirulina platensis*

A specific embodiment for the preparation of $^{13}$C-labeled biomass using *Spirulina platensis* will now be described in detail.

Preparation of Metals Medium

A trace metals medium was prepared using the materials listed in Table 2, and was used in both the inoculum and general medium described below. The materials listed on Table 2 were combined in a 1 L flask with cap, and were stirred until all materials were dissolved in solution. The pH of the solution was then adjusted to 6.5 using 2.0 N Sodium Hydroxide. The solution was diluted to 1.0 L using deionized water, and the filled flask was then autoclaved.

TABLE 2

| Metals Preparation | |
| --- | --- |
| Deionized Water | 500 mL |
| Zinc Sulfate | 111 mg |
| Cobalt Nitrate | 21.8 mg |
| Sodium Molybdate | 12.6 mg |
| Copper Sulfate | 40.0 mg |
| Boric Acid | 1.45 g |
| Manganese Sulfate | 0.77 g |
| Ferrous Sulfate | 5.00 g |
| Disodium EDTA | 51.00 g |

Preparation of a *Spirulina platensis* Inoculum.

This inoculum was used to seed the larger *Spirulina platensis* cultures later in the biomass cultivation process. The materials listed in table 3 were combined in a 10 L carboy flask, stirred until they dissolved, and diluted to obtain a total volume of 7 L using deionized water. 150 mL of the medium thus prepared was then placed into each of five 250 mL flasks and sealed using caps with foam plugs. 1.5 L of medium was then placed in each of four 2 L flasks and sealed with solid caps. If required for subsequent inoculum production, 10 ml of medium may be dispensed into 20 ml screw-caped test tubes. While not necessary for the present invention, it is desirable to use source inoculum that has already been $^{13}$C-labeled in order to obtain the highest possible levels of $^{13}$C incorporation into the biomass. The tubes and flasks were then autoclaved. The autoclaved flasks were then stored in relative darkness (100–300 Lux) at a temperature of 20–25° C. until used.

TABLE 3

| Inoculum Preparation | |
| --- | --- |
| Deionized Water | 6 Liters |
| Metals Mix | 14 mL |
| Mono-Potassium Phosphate | 2.67 g |
| Sodium Nitrate | 17.25 g |
| Potassium Chloride | 2.98 g |
| Sodium Chloride | 7.00 g |
| Magnesium Sulfate | 1.40 g |
| Calcium Chloride | 0.28 g |
| [$^{13}$C]-Sodium Bicarbonate | 56.20 g |

Using aseptic technique, the autoclaved 20 mL tubes were inoculated with 1–2 mL of source inoculum (desirably available from a previous production run, and containing *Spirulina platensis* algae). The 250 mL flasks were also inoculated at this time with 10–50 mL of source inoculum. The tubes and flasks were then incubated for 1–2 weeks at 25–30° C., with 2250–2750 Lux illumination, and at a rotation rate of 125–175 rpm. Caps with foam plugs may be used to allow for oxygen escape. The contents of four of the 250 mL flasks were then transferred, using aseptic technique, to the four 2 L flasks, while the remaining 250 mL flask was stored in relative darkness (100–300 Lux) at a temperature of 20–25° C. until used as source inoculum. The 2 L flasks were then incubated for 7–10 days at 7200–8800 Lux, 25–30° C., and at a rotation rate of 125–175 rpm. Two days prior to use in growth reactors, a total aerobic test was performed on each 2 L flask to assure they have remained uncontaminated.

TABLE 4

General Medium Preparation

| | |
|---|---|
| Deionized Water | 16 Liters |
| Zarrouk Metals Mix | 35 mL |
| Mono-Potassium Phosphate | 6.67 g |
| Sodium Nitrate | 43.13 g |
| Potassium Chloride | 7.44 g |
| Sodium Chloride | 17.49 g |
| Magnesium Sulfate | 3.50 g |
| Calcium Chloride | 0.70 g |

Preparation of Growth Medium.

The reagents listed in Table 4 were added to each of four 20 L autoclaved carboys, used for growth medium preparation and not to be confused with identical carboys that will be used as growth reactors, in the order listed in the table. The solids were stirred until they are completely dissolved in solution. [$^{13}$C]-sodium bicarbonate was then stirred into each carboy; while the amount may be varied, 140.3 g was used. One may determine the amount of [$^{13}$C]-sodium bicarbonate needed for a chosen density of biomass by utilizing the following formula: grams of NaH$^{13}$CO$_3$ needed=(g/L algae desired−0.2)(volume in carboy)/efficiency×(algae carbon content)/0.153). Approximately 250 mL of 2 N sodium hydroxide was then added in stepwise fashion to adjust the pH to 9.5. The growth medium prep carboys were set aside until just prior to inoculation of the growth reactors. The contents of each were sterile filtered and pumped into each corresponding growth reactor just prior to inoculation.

Preparation of $^{13}$C-Labeled BioMass

Four carboy growth reactors that had been autoclaved, were filled with growth medium. The medium was transferred from the four medium-filled 20 L carboys to the four prepared carboy growth reactors, by means of a peristaltic pump through an autoclaved medium fill line, at a rate of 0.6–0.8 L/min. For sterility, the fill line was equipped with a sterile filter. The filter used was a 0.22 micron Polycap AS filter but any suitable commercial filter can be used. Once the carboy growth reactors were filled with growth medium, they were seeded with biomass culture from the inoculation vessel.

Using aseptic technique, ¼$^{th}$ of the pooled inoculum from the inoculation vessel was transferred to each carboy growth reactor through the dosing port. Growth reactors that were prepared as described above were stored (desirably for no more than 2 days), in relative darkness (100–300 Lux) at a temperature of 20–25° C.

The four growth reactor carboys were then placed on a rotary shaker table assembly, such as the one illustrated in FIGS. 4 and 5. The rotary shaker table assembly was one provided by Gump Rotary Shaker Systems Inc., Savannah Ga. The shaker platform was rotated at about 80 rpm, in order to maintain even lighting and temperature within the carboy growth reactors.

Heaters were used monitored by temperature probes to maintain the temperature in the carboy growth reactors in the range of 29–31° C. 16" oscillating stand fans, were placed strategically around the rotary shaker table assembly in order to maintain an even temperature throughout the system.

Once the rotary shaker table assembly was set up and in operation, in-process sampling and testing was conducted at regular intervals to determine the level of growth, whether or not appropriate growth conditions were being maintained, and to detect possible contamination. In-process sampling, through the sample line, was initiated when the growth reactor carboys became opaque due to biomass growth. Samples were tested for pH, appearance, density, the presence of aerobic bacteria, and the presence of yeast and/or mold. The medium within the carboy growth reactors was maintained at a pH between about 9.5 and 10.5. 1M mono-potassium phosphate buffer was added as necessary when the pH thresholds were exceeded.

A nitrogen purge was conducted four times daily. Nitrogen purge at a gas flow rate of 2 L per minute for 5 minutes provides useful purging.

Harvesting of the biomass was initiated when the culture reached a density of approximately >2.2 g/L, or 40–44 grams of biomass per carboy.

The biomass was harvested using the apparatus shown in FIG. 6 and described above. The Szenti-Gyorgyi & Blum Continuous flow With Pelleting Rotor Insert (KSB CFWP), was used within a Sorvall Centrifuge with a fixed-angle rotor. During harvesting, a centrifuge rotation rate of about 4500–5500 rpm was used. Flow through the tubing was regulated using adjustable pinch clamps, and connections to other tubing sections were accomplished using ¼" I. D. Kynar couplers.

During final processing, a biomass slurry was prepared, poured into shallow containers, frozen, and subsequently lyophilized. As with all other processing steps, operations were conducted under sanitary conditions, under laminar-flow hoods, with the operators wearing protective clothing. Two 1-gallon shallow containers were used for each carboy harvested, which generally resulted in about 600 grams of biomass slurry being placed in each container. Deionized water was added to the centrifuged biomass and vigorously shaken to create a slurry. Approximately 100 ml was required per centrifuge bottle, resulting in a solution that is about 3% biomass by weight. The slurry from a number of centrifuge bottles was combined and stirred until free of lumps, and the density of the combined slurry determined. After cleaning and inserting a liner into the pre-lyophilization containers, the slurry was poured into the containers, resulting in a layer about ½" thick. The containers were then covered with lids, and stacked in a dedicated freezer at −10 to −25° C. Aluminum spacers were used between the containers to enhance air circulation.

The frozen algal cakes were then removed from the 1-gallon containers, placed on pre-chilled anodized aluminum lyophilization trays, inserted into a suitable lyophilizer, and lyophilized to meet a loss on drying (LOD) specification of 2–4%. The freeze dry cycle lasted approximately 28 hours with temperature starting at −20° C. and going to a final product temperature of 55° C. with a pressure of <200 microns. Lyophilization resulted in a dried biomass with very low water activity. The lyophilized biomass was removed when dry and milled through a 500 and 250 μM mesh screen to yield relatively consistent particle size. The labeled biomass was at this point suitable for use as a bulk drug.

The purity of the product was determined in this example with Combustion analysis to determine the carbon content and Gas Isotope Ratio Mass Spectroscopy to determine the amount of isotope label present.

While a specific embodiment of the present invention has been described, it should be understood that various changes, adaptations and modifications might be made therein without departing from the spirit of the invention and the scope of the appended claims.

What is claimed is:

1. A method of preparing a bulk drug comprising a biomass that is substantially uniformly labeled with carbon-13 comprising:
   a) providing a growth medium comprising a water-soluble carbon-13 labeled carbon source;
   b) inoculating the growth medium contained in a growth reactor with an organism which will uptake carbon through photosynthesis, wherein the sole source of carbon provided to the growth reactor is the water-soluble carbon-13 labeled carbon source;
   c) growing and monitoring the growth of the organism until a predetermined biomass density is obtained;
   d) harvesting the carbon-13 labeled biomass; and
   e) incorporating some or all of the carbon-13 labeled biomass into a bulk drug.

2. The method of claim 1 wherein said water-soluble carbon source is a [$^{13}$C]-bicarbonate or [$^{13}$C]-carbonate salt.

3. The method of claim 1 wherein said water-soluble carbon source is [$^{13}$C]-sodium bicarbonate.

4. The method of claim 1 wherein the organism is an alga.

5. The method of claim 4 wherein the alga is an edible alga species.

6. The method of claim 5 wherein the alga is of the species *Spirulina platensis*.

7. The method of claim 1 further comprising lyophilizing the harvested biomass.

8. The method of claim 7 further comprising milling the biomass into a bulk drug form.

9. The method of claim 1 wherein greater than 90% of the carbon in the harvested biomass is labeled with a carbon-13 isotope.

10. The method of claim 4 wherein the organism used as an inoculum is a substantially pure uni-algal inoculum.

11. The method of claim 1 wherein the growth medium is illuminated using a pass-through illumination of about 1000–2000 Lux and maintained at a temperature of about 29–31° C. during the growth process and the growth medium has a pH of approximately 10.

* * * * *